United States Patent [19]

Feathers et al.

[11] Patent Number: 5,149,892
[45] Date of Patent: Sep. 22, 1992

[54] CHLORINATED BENZENES

[75] Inventors: Robert E. Feathers, Irwin, Pa.; J. Douglas Mansell, Sulphur, La.

[73] Assignee: PPG Industries, Inc., Pittsburgh, Pa.

[21] Appl. No.: 782,006

[22] Filed: Oct. 22, 1991

[51] Int. Cl.$^5$ .................. C07C 17/12; C07C 25/00
[52] U.S. Cl. .................. 570/210; 570/206; 570/207; 570/208
[58] Field of Search .............. 570/207, 208, 210, 206

[56] References Cited

U.S. PATENT DOCUMENTS

| | | | |
|---|---|---|---|
| 2,081,322 | 5/1937 | Carney | 23/263 |
| 4,215,011 | 7/1980 | Smith, Jr. | 252/426 |
| 4,232,177 | 11/1980 | Smith, Jr. | 585/324 |
| 4,242,530 | 12/1980 | Smith, Jr. | 585/510 |
| 4,260,052 | 2/1981 | Smith, Jr. | 252/126 |
| 4,302,356 | 11/1981 | Smith, Jr. | 252/426 |
| 4,306,068 | 12/1981 | Smith, Jr. | 546/184 |
| 4,307,254 | 12/1981 | Smith, Jr. | 568/697 |
| 4,332,968 | 6/1982 | Smith, Jr. | 564/278 |
| 4,336,407 | 6/1982 | Smith, Jr. | 568/697 |
| 4,375,576 | 3/1983 | Smith, Jr. | 585/510 |
| 4,439,350 | 3/1984 | Smith, Jr. | 502/527 |
| 4,443,559 | 4/1984 | Smith, Jr. | 502/527 |
| 4,447,668 | 5/1984 | Smith, Jr. et al. | 585/639 |
| 4,482,775 | 11/1984 | Smith, Jr. | 585/671 |
| 4,504,687 | 3/1985 | Jones, Jr. | 568/697 |
| 4,510,336 | 4/1985 | Hearn | 568/697 |
| 4,536,373 | 8/1985 | Jones, Jr. | 422/211 |
| 4,551,567 | 11/1985 | Smith, Jr. | 568/907 |
| 4,570,023 | 2/1986 | Petruck et al. | 570/210 |
| 4,629,710 | 12/1986 | Smith, Jr. | 502/11 |
| 4,748,287 | 5/1988 | Rohlk et al. | 570/209 |
| 4,822,933 | 4/1989 | Suzuki | 570/208 |
| 4,835,327 | 5/1989 | Milam et al. | 570/208 |
| 4,849,569 | 7/1989 | Smith, Jr. | 585/446 |
| 4,914,247 | 4/1990 | Sekizawa et al. | 570/208 |
| 4,918,243 | 4/1990 | Smith, Jr. et al. | 568/697 |
| 4,950,803 | 8/1990 | Smith, Jr. et al. | 568/697 |
| 4,950,834 | 8/1990 | Arganbright et al. | 585/446 |
| 4,978,807 | 12/1990 | Smith, Jr. | 568/697 |
| 4,982,022 | 1/1991 | Smith, Jr. et al. | 568/899 |
| 4,990,706 | 2/1991 | Laukonen | 570/208 |
| 5,001,290 | 3/1991 | Hillman et al. | 570/210 |
| 5,003,124 | 3/1991 | Smith et al. | 585/526 |

OTHER PUBLICATIONS

Kirk-Othmer, *Encyclopedia of Chemical Technology* (2nd Edition), vol. 5, pp. 253-263 (1964).
Kirk-Othmer, *Encyclopedia of Chemical Technology* (3rd Edition), vol. 5, pp. 797-808 (1979).
L. A. Smith et al, "Catalytic Distillation—A New Chapter in Unit Operations"—Aiche, Houston, (Spring 1991).

*Primary Examiner*—Werren B. Lone
*Attorney, Agent, or Firm*—George D. Morris

[57] ABSTRACT

Benzene or a chlorinated benzene feedstock compound represented by the formula $C_6H_{6-x}Cl_x$ is chlorinated in the rectifying zone of a catalytic distillation reactor to produce a chlorinated benzene product compound represented by the formula $C_6H_{5-x}Cl_{x+1}$, where x is an integer in the range of from 0 to 5.

17 Claims, 2 Drawing Sheets

CHLORINATED BENZENES

BACKGROUND OF THE INVENTION

Chlorinated benzenes are frequently produced by chlorinating benzene or chlorinated benzenes of lower chlorine content in the presence of a catalyst. The formation of the desired chlorinated benzene is accompanied by the formation of various by-products such as more highly chlorinated benzenes. Often isomer(s) of the desired chlorinated benzene, degradation products, and/or some "heavies" (i.e., polychlorinated cyclohexanes, polychlorinated cyclohexenes, and/or polychlorinated cyclohexadienes) are also produced as by-products. In many instances once the desired amount of the desired chlorinated benzene (usually, but not necessarily close to the maximum yield attainable) has been produced, the chlorination is terminated in order to conserve chlorinating agent and to maintain at tolerably low levels the production of undesirable higher chlorinated benzenes and other by-products.

In most instances the formation of by-products is undesirable since the by-products are of lesser value economically and since they often result in disposal problems.

THE INVENTION

A method has now been discovered in which chlorinated benzene of a desired degree of chlorination may be produced with improved selectivity. In some instances a desired chlorinated benzene isomer may be produced with improved selectivity.

Accordingly, in the method wherein a benzenoid feedstock compound represented by the formula $C_6H_{6-x}Cl_x$ is chlorinated in the presence of a chlorination catalyst in a chlorination system to produce a benzenoid product compound represented by the formula $C_6H_{5-x}Cl_{x+1}$, where x is an integer in the range of from 0 to 5, the improvement wherein: (a) the chlorination system comprises a rectifying zone and a stripping zone, (b) the rectifying zone contains chlorination catalyst, (c) the feedstock compound is introduced to the chlorination system, (d) molecular chlorine is introduced to the top of the stripping zone, (e) the feedstock compound is countercurrently contacted in the rectifying zone with molecular chlorine, (f) overhead vapor from the rectifying zone is partially condensed to provide a liquid phase comprising liquid feedstock compound and a gaseous phase comprising hydrogen chloride, (g) substantially all of the liquid phase is introduced as reflux to the rectifying zone, (h) the gaseous phase is removed from the chlorination system, (i) liquid from the rectifying zone is countercurrently contacted in the stripping zone with reboiled vapors of the product compound, and (j) the product compound is removed from the stripping zone.

As used herein, "conversion" is the percentage of first benzenoid feedstock compound converted to other compounds during the reaction, "selectivity" is the ratio of the moles of the desired benzenoid product compound produced to the moles of the benzenoid feedstock compound converted to all products of the reaction, expressed as percent, and "yield" is the product of "conversion" and "selectivity" divided by one hundred.

Although it is not desired to be bound by any theory, it is believed that the improvement in selectivity is likely due to conducting the chlorination reaction under conditions where the product compound, once formed, is quickly removed from the region of chlorination. The normal boiling points of compounds having the empirical formula $C_6H_{6-x}Cl_x$ increase with increasing values of x. The chlorination may therefore be conducted in a distillation environment where the higher boiling point of the benzenoid product compound (which has one more chloro group than the benzenoid feedstock compound) causes it to quickly descend from a rectifying zone where chlorination is taking place to a stripping zone which, except for the uppermost portion where chlorine is introduced, is deficient in chlorine. The method of the invention in the first instance promotes the selectivity of product having one more chloro group than the feedstock, without regard to isomers. In many cases, however, the differences in boiling points between chlorinated benzene isomers having the same empirical formula is great enough that the method of the invention sometimes promotes the formation of one isomer over another. Isomeric selectivity can also be increased in some instances by utilizing a chlorination catalyst which favors formation of one or more particular isomers.

DESCRIPTION OF THE DRAWING

For a better understanding of the invention, reference may be made to the drawings wherein like numerals refer to like parts and in which.

The particular form of apparatus used in practicing the invention may vary widely. Usually, but not necessarily, the rectifying zone and the stripping zone are contained in the same distillation column in which vapor from the top of the stripping zone is allowed to pass upward into the rectifying zone and liquid from the bottom of the rectifying zone is allowed to pass downward into the top of the stripping zone. Examples of various columns that may be used include bubble cap columns, sieve plate columns, packed columns, and similar devices. In all cases the lowest chlorine feed point is considered to be a part of the stripping zone.

Figure 1:
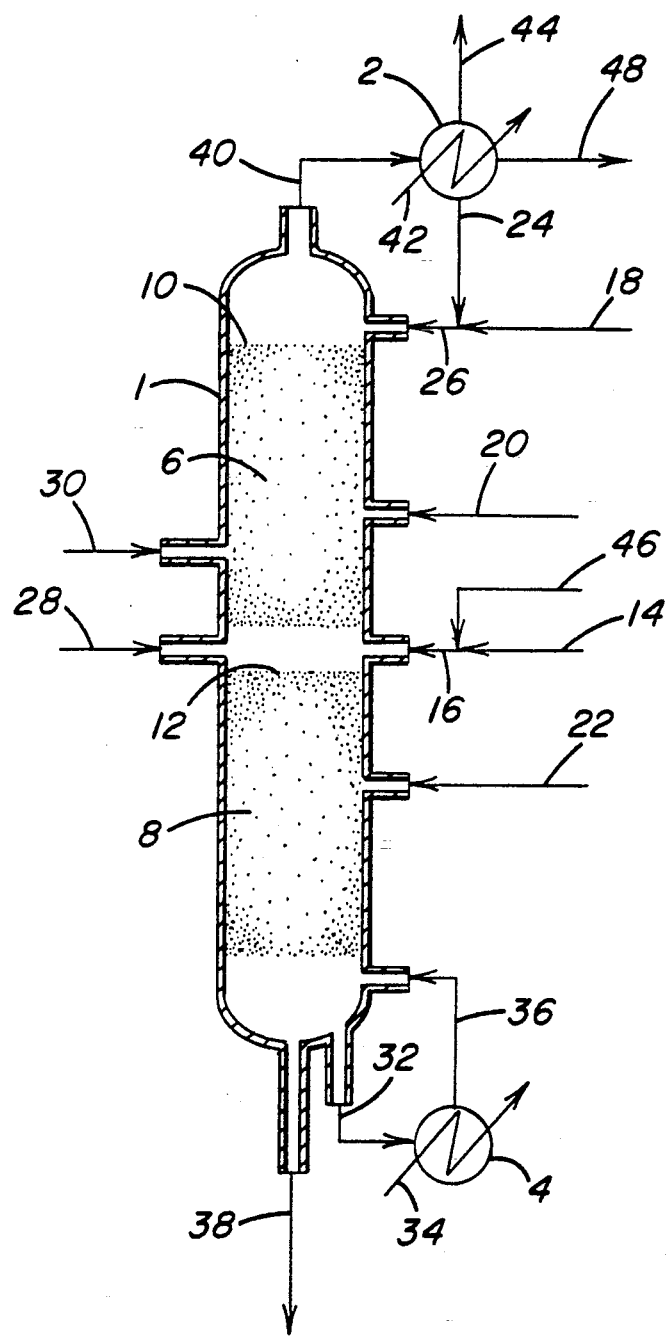
FIG. 1 shows diagrammatically an embodiment of the invention.

Referring now in detail to the drawings, there is shown diagrammatically in FIG. 1 a chlorination system comprising column 1, condenser 2, reboiler 4, and associated piping. Column 1 comprises rectifying zone 6 and stripping zone 8. Rectifying zone 6 contains packing material 10 while stripping zone 8 contains packing material 12. Benzene or a chlorinated benzene feedstock is introduced to column 1 through line 14 and line 16. The benzene or chlorinated benzene feedstock may alternatively or additionally be introduced at other locations such as, for example, through line 18 and line 26, through line 20, and/or through line 22. Friedel-Crafts chlorination catalyst or precursor thereof dissolved or suspended in the benzene or chlorinated benzene feedstock may, when used, be introduced through line 14 and line 16, through line 18 and line 26, and/or through line 20. Condensate passing through line 24 is combined with feedstock, if any, passing through line 18 to form the stream passing through line 26. The stream passing through line 26 is introduced to column 1 as reflux. Molecular chlorine is introduced to column 1 through line 28. Additional molecular chlorine may optionally be introduced through one or more additional lines such as line 30. Bottoms liquid is passed through line 32 to reboiler 4 heated by steam or other hot heat transfer fluid introduced to line 34. In reboiler 4 the bottoms liquid is boiled, thereby producing reboiled vapor which returns to column 1 through line 36. A portion of the bottoms liquid, which comprises chlorinated benzene product, is removed through line 38 for such use as may be desired. Vapor from the rectifying zone is passed through line 40 and introduced to condenser 2 which is cooled by coolant passing through line 42. In condenser 2 the vapor is partially condensed to a liquid. The uncondensed vapor which remains and which is mainly hydrogen chloride, is removed through line 44. Substantially all of the condensate from condenser 2 is introduced to column 1 as reflux; however, a small amount of the condensate may be purged through line 48 whenever it is necessary or desirable to remove one or more low boiling materials which would otherwise tend to accumulate in the upper part of the chlorination system. When purging of some of the condensate is practiced, it may be accomplished intermittently or continuously, as desired.

Rectifying zone 6 contains chlorination catalyst. Various chlorination catalysts may be used and they may be present in a wide variety of forms.

The preferred chlorination catalysts are the Friedel-Crafts inorganic metal halide chlorination catalysts. Examples of these include ferric chloride, aluminum chloride, antimony chloride, and stannic chloride. The Friedel-Crafts inorganic metal halide chlorination catalysts may be introduced directly or in many instances they may be generated in situ from one or more precursors. Examples of such precursors include metallic iron, ferrous chloride, ferrous sulfate, metallic aluminum, and stannous chloride. The Friedel-Crafts inorganic metal halide chlorination catalyst or its precursor may be introduced to the chlorination system at any convenient location which will maintain Friedel-Crafts inorganic metal halide chlorination catalyst within the rectifying zone. The especially preferred chlorination catalyst is ferric chloride.

Figure 2:
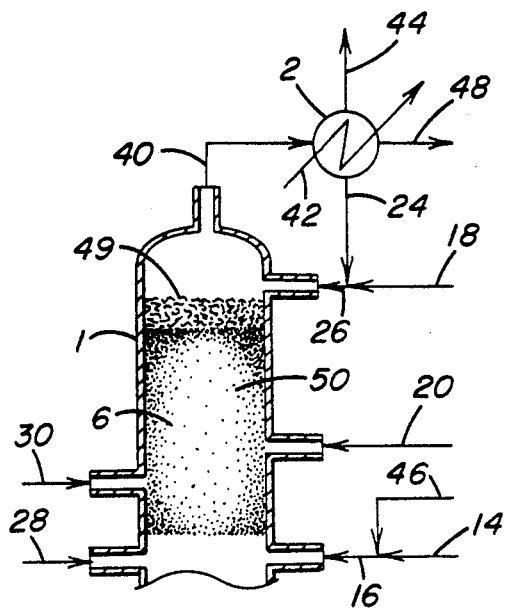
FIG. 2 shows diagrammatically a modification which can be made to the embodiment of FIG. 1.
Figure 3:
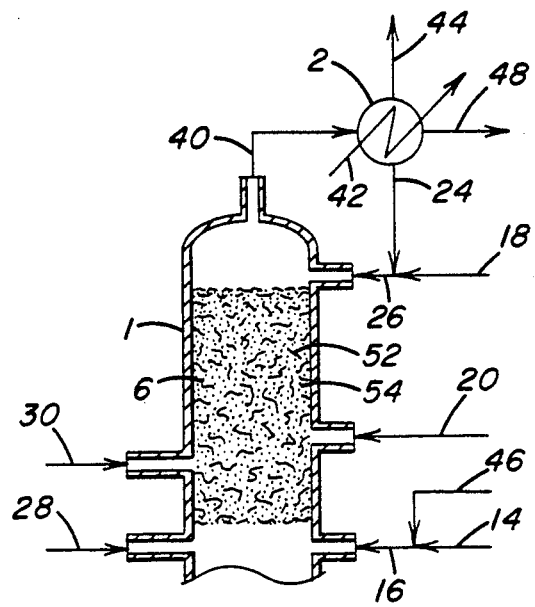
FIG. 3 shows diagrammatically another modification which can be made to the embodiment of FIG. 1.
Figure 4:
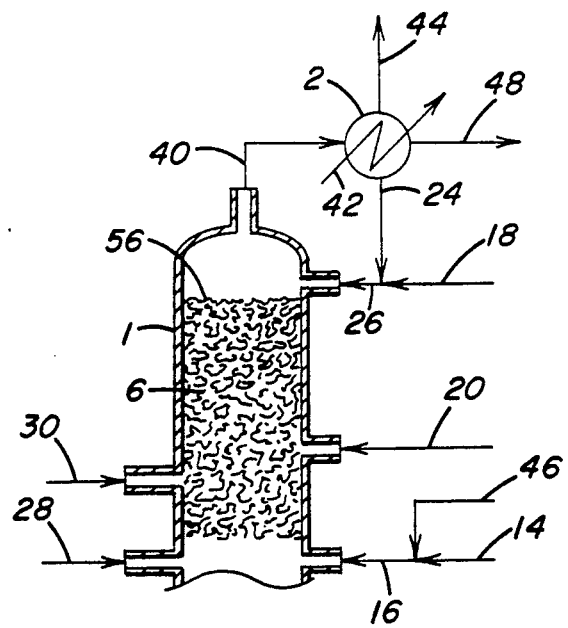
FIG. 4 shows diagrammatically yet a further modification which can be made to the embodiment of FIG. 1.

When ferric chloride is employed as the catalyst, it may be dissolved or suspended in the benzene or chlorinated benzene feedstock and introduced through line 14 and line 16, through line 18 and line 26, and/or through line 20. Alternatively, the ferric chloride may be generated in situ from iron or steel turnings which comprise some or all of the packing material 10. One such alternative is shown diagrammatically in FIG. 2 where iron or steel turnings 49 are positioned atop inert packing material 50. Another alternative is shown diagrammatically in FIG. 3 where iron or steel turnings 52 are admixed with inert packing material 54. Yet another alternative is shown in FIG. 4 where iron or steel turnings 56 constitute substantially all of the packing material in rectifying zone 6. Although iron or steel turnings are preferred because of their low cost, other shapes can be used, as for example, iron or steel Raschig rings, Berl saddles, punchings, coupons, wires, and the like. From time to time the iron or steel turnings or other shapes are replenished through a port (not shown) in column 1. A rather extreme, but nevertheless viable, alternative is to fabricate at least the upper portion of the shell of column 1 from iron or steel and allow the necessary ferric chloride to be generated by corrosion of the shell.

When ferric chloride or other Friedel-Crafts inorganic metal halide is employed as the chlorination catalyst, it tends to migrate down the column with the product and to be withdrawn from the system through line 38. The material withdrawn through line 38 may, when desired, be forwarded to a purification system of conventional design where the product may be further purified. In the course of purifying the product, the Friedel-Crafts inorganic metal halide chlorination catalyst may be recovered and, when desired, recycled to column 1 for further use as a chlorination catalyst.

Other chlorination catalysts may be used in lieu of the Friedel-Crafts chlorination catalysts. Examples include zeolite L and zeolite Y which may be fabricated into various shapes and used as all or a portion of packing material 10. These zeolites tend to favor formation of certain isomers in some chlorinations; see for example, U.S. Pat. No. 4,835,327, the entire disclosure of which is incorporated herein by reference.

The above listing of chlorination catalysts is illustrative only and not exhaustive; other chlorination catalysts may be used.

The amount of chlorination catalyst present may be widely varied. The amount used depends upon many factors including, but not limited to: the identity and activity of the catalyst; the composition of the benzenoid feedstock; the presence, identities, and concentrations, if any, of catalyst poisons or inhibitors; the presence, identities, and concentrations, if any, of catalytic promoters; the manner in which the desired catalyst concentration is maintained in the rectifying zone; and the solubility of the catalyst in the organic liquid present in the rectifying zone. In general the chlorination catalyst should be present in at least a catalytic amount. Amounts of chlorination catalyst in excess of that needed to catalyze the reaction are usually inconsequential. When Friedel-Crafts inorganic metal halide chlorination catalyst is used, the catalyst concentration is most often in the range of from about 100 to about 2000 parts of Friedel-Crafts inorganic metal halide chlorination catalyst per million parts of organic liquid, by weight. From about 200 to about 1500 parts of Friedel-Crafts inorganic metal halide chlorination catalyst per million parts of organic liquid, by weight is preferred. When zeolite chlorination catalyst is used, the amount employed may vary extremely widely since it is insoluble in the organic liquid; in general it is used in at least a catalytic amount, but because of its insolubility, large excesses may be used.

One or more promoters such as sulfur monochloride ($S_2Cl_2$) or sulfur dichloride ($SCl_2$), and/or one or more promoter precursors such as elemental sulfur, carbon disulfide or sulfur dioxide, may optionally be introduced to the chlorination system at any convenient location which will maintain promoter within the rectifying zone. Promoter and/or promoter precursor may, for example, be introduced through line 46 and line 16. The amount of promoter present may vary widely and depends upon many factors similar to those described above in respect to the chlorination catalyst. When promoter is used, the promoter concentration is ordinarily in the range of from about 0.01 to about 100 parts of promoter per million parts of organic liquid, by weight. From about 1 to about 50 parts of promoter per million parts of organic liquid, by weight, is preferred.

Descending liquid is countercurrently contacted in rectifying zone 6 with molecular chlorine introduced to the system through line 28 (and optionally through one or more additional lines such as line 30) and with vapor ascending from stripping zone 8. The normal boiling point of molecular chlorine is much lower than those of the organic materials present in column 1. This, together with the temperature gradient existing lengthwise through the column in accordance with the known principles of distillation, causes the molecular chlorine to ascend into the rectifying zone where it can react with the feedstock and to leave all but the very uppermost portion of the stripping zone substantially free of molecular chlorine. Since the boiling point of the chlorinated product is higher than that of the feedstock, the chlorinated product is encouraged by the temperature gradient to rapidly descend from the rectifying zone into the interior of the stripping zone where conditions do not favor further chlorination.

Inasmuch as the invention promotes selectivity in the first instance by providing conditions which discourage chlorination of the desired product to higher levels of chlorination, it is preferred that the feedstock be of as high a purity as practicable. Nevertheless, mixtures of various benzenoid compounds may be used. In some instances the presence of other benzenoid compounds may somewhat reduce the selectivity attained. In others, however, such as when the desired feedstock compound is much more susceptible to chlorination than another compound, any reduction in selectivity is minimal. The preferred feedstock compounds are selected from benzene, monochlorobenzene, ortho-dichlorobenzene, meta-dichlorobenzene, and para-dichlorobenzene. It follows that the preferred value of x in the empirical formula $C_6H_{6-x}Cl_x$, discussed above, is 0, 1, or 2.

The pressure at which the method of the invention is conducted may vary widely. It may be subatmospheric, ambient atmospheric, or superatmospheric. In most cases it is at about ambient atmospheric pressure or a little higher. In many cases the pressure is in the range of from about −70 to about +690 kilopascals, gauge. Preferably the pressure is in the range of from about 0 to about 345 kilopascals, gauge.

The temperatures at which the method of the invention is conducted may vary considerably. In general, there is a temperature gradient longitudinally through the column in accordance with the general principles of distillation. The temperature at any location in the column is the boiling point of the composition at that location under the prevailing pressure. Usually, but not necessarily, the temperatures are in the range of from about 40° C. to about 320° C. From about 80° C. to about 230° C. is preferred.

For the sake of clarity in setting forth the nature of the invention, parts of the apparatus such as valves, pumps, flow indicators, pressure indicators, temperature indicators, hold-up tanks, storage tanks, and the like, not essential to a complete understanding of the invention, have been omitted from the drawings.

It will be appreciated that various modifications can be made to the systems of the drawings without departing from the spirit of the invention. For example, the distillation column may be a bubble cap column, sieve plate column, or similar device. Solid catalyst or catalyst precursors may be placed in containers which are placed above the trays of a distillation column in accordance with the general principles of U.S. Pat. No. 4,232,177; 4,307,254; 4,439,350; 4,443,559; 4,536,373; and 4,950,834, the disclosures of which are, in their entireties, incorporated herein by reference.

Although the preferred mode of operation is continuous, it will be appreciated that the chlorination can be conducted semi-batchwise or semi-continuously.

The invention is further described in conjunction with the following example which is to be considered illustrative rather than limiting.

EXAMPLE

A glass distillation column having an internal diameter of about 2.54 centimeters and comprising two sections with a feed point between the two sections was packed with 189.6 grams of 6.4-millimeter ceramic saddles in the bottom section and 186.1 grams of 6.4-millimeter ceramic saddles in the top section. The height of the packing in each section was in the range of from about 45 to about 51 centimeters. Iron wire weighing approximately ½ gram was located in the upper 15 centimeters of the packing in the upper section. A condenser set for total reflux was attached to the top of the column. A scrubber was attached to the condenser such that uncondensed gases passing through the condenser were scrubbed in the scrubber. A pot containing 200 grams of para-dichlorobenzene feedstock was placed in an electric heating mantle and connected to the bottom of the distillation column. Gas chromatographic analysis showed the para-dichlorobenzene feedstock to contain 99.72 area percent para-dichlorobenzene, 0.04 area percent ortho-dichlorobenzene, 0.23 area percent trichlorobenzene, and zero area percent tetrachlorobenzenes. Extraordinary attention was given to the exclusion of light. The column was traced with heating tape, and then wrapped sequentially with insulation and aluminum foil. Aluminum foil was applied in layers over the pot, the condenser and the exit lines.

Molecular chlorine was fed at a rate of approximately 4.4 grams per hour. After chlorinating the feedstock for 5 ½ hours, black iron turnings were placed atop the ceramic saddles in the top section of the column such that the depth of the iron turnings was about 2.5 centimeters. The introduction of molecular chlorine at a rate of approximately 4.4 grams per hour was then resumed. Inasmuch as the column was not operated overnight, the chlorination was conducted intermittently. The operating conditions are shown in Table 1. analyses of samples taken from the pot and the Tri/Tetras Mole Ratio are shown in Table 2.

TABLE 1

| Cumulative Time, hours | Temperature, °C. | | | |
| --- | --- | --- | --- | --- |
| | Pot | Below Feed Point | Above Feed Point | Top of Column |
| 0 | 175 | 173 | 173 | 173 |
| 4.75 | 176 | 173 | 172 | 172 |
| 8.5 | 180 | 173 | 172 | 171 |
| 11.0 | 184 | 173 | 172 | 170 |
| 14.75 | 193 | 174 | 172 | 170 |
| 18.0 | 200 | 175 | 171 | 162 |
| 20.0 | 207 | 177 | 172 | 145 |
| 21.0 | 209 | 176 | 169 | 100 |

TABLE 2

| Cumulative Time, hours | Gas Chromatographic Analysis, area percent | | | | | Tri/Tetras Mole Ratio |
|---|---|---|---|---|---|---|
| | Para-$C_6H_4Cl_2$ | Ortho-$C_6H_4Cl_2$ | $C_6H_3Cl_3$ | 1,2,4,5-$C_6H_2Cl_4$ | 1,2,3,4-$C_6H_2Cl_4$ | |
| 0 | 99.72 | 0.04 | 0.23 | 0 | 0 | — |
| 4.75 | 95.92 | 0.05 | 4.00 | 0.01 | 0.02 | — |
| 8.5 | 86.56 | 0 | 13.30 | 0.10 | 0.04 | 72.4 |
| 11.0 | 76.18 | 0 | 23.51 | 0.21 | 0.11 | 62.9 |
| 14.75 | 48.62 | 0 | 50.53 | 0.57 | 0.28 | 55.1 |
| 18.0 | 37.82 | 0 | 61.01 | 0.78 | 0.39 | 50.9 |
| 20.0 | 19.31 | 0 | 78.78 | 1.29 | 0.62 | 48.0 |
| 21.0 | 16.29 | 0 | 81.66 | 1.39 | 0.67 | 45.5 |

On a mole basis, 89 percent of the expected hydrogen chloride was found in the scrubber.

Although the present invention has been described with reference to specific details of certain embodiments thereof, it is not intended that such details should be regarded as limitations upon the scope of the invention except insofar as they are included in the accompanying claims.

I claim:

1. In the method wherein a benzenoid feedstock compound represented by the formula $C_6H_{6-x}Cl_x$ is chlorinated in the presence of a chlorination catalyst in a chlorination system to produce a benzenoid product compound represented by the formula $C_6H_{5-x}Cl_{x-1}$, where x is an integer in the range of from 0 to 5, the improvement wherein:
   (a) said chlorination system comprises a rectifying zone and a stripping zone;
   (b) said rectifying zone contains chlorination catalyst;
   (c) said feedstock compound is introduced to said chlorination system;
   (d) molecular chlorine is introduced to the top of said stripping zone;
   (e) said feedstock compound is countercurrently contacted in said rectifying zone with molecular chlorine;
   (f) overhead vapor from said rectifying zone is partially condensed to provide a liquid phase comprising liquid feedstock compound and a gaseous phase comprising hydrogen chloride;
   (g) substantially all of said liquid phase is introduced as reflux to said rectifying zone;
   (h) said gaseous phase is removed from said chlorination system;
   (i) liquid from said rectifying zone is countercurrently contacted in said stripping zone with reboiled vapors of said product compound; and
   (j) said product compound is removed from said stripping zone.

2. The method of claim 1 wherein said catalyst is zeolite L.

3. The method of claim 1 wherein said catalyst is zeolite Y.

4. The method of claim 1 wherein said catalyst is Friedel-Crafts inorganic metal halide chlorination catalyst.

5. The method of claim 1 wherein said catalyst is ferric chloride.

6. The method of claim 5 wherein said ferric chloride is generated within said rectifying zone by the corrosion of iron or steel.

7. The method of claim 6 wherein said iron or steel is iron or steel turnings.

8. The method of claim 6 wherein said iron or steel is positioned atop inert packing material.

9. The method of claim 8 wherein said benzenoid feedstock compound is selected from the group consisting of benzene, monochlorobenzene, ortho-dichlorobenzene, meta-dichlorobenzene, and para-dichlorobenzene.

10. The method of claim 1 wherein the chlorination reaction is conducted in the presence of promoter.

11. The method of claim 10 wherein said promoter is sulfur monochloride, sulfur dichloride, or a mixture thereof.

12. The method of claim 1 wherein said benzenoid feedstock compound is selected from the group consisting of benzene, monochlorobenzene, ortho-dichlorobenzene, meta-dichlorobenzene, and para-dichlorobenzene.

13. The method of claim 5 wherein said benzenoid feedstock compound is selected from the group consisting of benzene, monochlorobenzene, ortho-dichlorobenzene, meta-dichlorobenzene, and para-dichlorobenzene.

14. The method of claim 5 wherein said benzenoid feedstock compound is para-dichlorobenzene.

15. The method of claim 14 wherein said ferric chloride is generated within said rectifying zone by the corrosion of iron or steel.

16. The method of claim 15 wherein the pressure is in the range of from about 0 to about 345 kilopascals, gauge.

17. The method of claim 16 wherein the temperature is in the range of from about 80° C. to about 230° C.

* * * * *

UNITED STATES PATENT AND TRADEMARK OFFICE
CERTIFICATE OF CORRECTION

PATENT NO. : 5,149,892

DATED : September 22, 1992

INVENTOR(S) : Robert E. Feathers et al

It is certified that error appears in the above-identified patent and that said Letters Patent is hereby corrected as shown below:

Cover page, first column, U.S. Patent Documents, "4,260,052" should be --4,250,052--.

Column 7, line 27, "$C_6H_{5-x}Cl_{x-1}$" should be --$C_6H_{5-x}Cl_{x+1}$--.

Signed and Sealed this

Sixteenth Day of November, 1993

*Attest:*

BRUCE LEHMAN

*Attesting Officer*     *Commissioner of Patents and Trademarks*